(12) United States Patent
Buckley et al.

(10) Patent No.: US 9,140,653 B2
(45) Date of Patent: Sep. 22, 2015

(54) SPARK EMISSION PARTICLE DETECTOR

(75) Inventors: Steven G. Buckley, Redmond, WA (US); Gregg A. Lithgow, Seattle, WA (US)

(73) Assignee: TSI Incorporated, Shoreview, MN (US)

( * ) Notice: Subject to any disclaimer, the term of this patent is extended or adjusted under 35 U.S.C. 154(b) by 90 days.

(21) Appl. No.: 13/878,416

(22) PCT Filed: Oct. 8, 2011

(86) PCT No.: PCT/US2011/055499
§ 371 (c)(1),
(2), (4) Date: Jun. 21, 2013

(87) PCT Pub. No.: WO2012/048308
PCT Pub. Date: Apr. 12, 2012

(65) Prior Publication Data
US 2013/0265574 A1 Oct. 10, 2013

Related U.S. Application Data

(60) Provisional application No. 61/391,478, filed on Oct. 8, 2010.

(51) Int. Cl.
*G01J 3/30* (2006.01)
*G01N 21/67* (2006.01)
(Continued)

(52) U.S. Cl.
CPC ............ *G01N 21/67* (2013.01); *G01N 15/0618* (2013.01); *G01N 15/0656* (2013.01); *F01N 11/00* (2013.01)

(58) Field of Classification Search
CPC ........... G01N 21/67–21/68; G01N 2001/2223; G01N 15/0606

USPC ...................... 356/313–318, 72, 73; 324/424; 250/281–300
See application file for complete search history.

(56) References Cited

U.S. PATENT DOCUMENTS

| 4,846,920 A | 7/1989 | Keller et al. |
|---|---|---|
| 4,925,307 A | 5/1990 | Cremers et al. |
| 5,153,519 A * | 10/1992 | Wentworth et al. ........... 324/464 |

(Continued)

FOREIGN PATENT DOCUMENTS

| WO | WO 2010/033452 A2 | 3/2010 |
|---|---|---|
| WO | WO 2011/006156 A2 | 1/2011 |

OTHER PUBLICATIONS

Notification of Transmittal of the International Search Report and the Written Opinion of the International Searching Authority, or the Declaration for International Application No. PCT/US2011/055499, dated Oct. 8, 2011, 12 pages.

*Primary Examiner* — Michael A Lyons
*Assistant Examiner* — Shawn Decenzo
(74) *Attorney, Agent, or Firm* — Patterson Thuente Pedersen, P.A.

(57) ABSTRACT

Techniques and devices are disclosed for detecting particle composition. In one aspect, a method performed by a detector to detect particles includes receiving particles at an aerosol inlet of the detector. The method includes carrying the received particles within a stream of gas and charging the particles within the stream of gas using a charger to have a charge. The method includes transporting the charged particles to a location of a collection electrode. The method includes biasing the collection electrode to a voltage using a high-voltage supply to attract either negatively or positively charged particles, and analyzing the particles.

20 Claims, 3 Drawing Sheets

(51) Int. Cl.
*G01N 15/06* (2006.01)
*F01N 11/00* (2006.01)

(56) References Cited

U.S. PATENT DOCUMENTS

| | | | |
|---|---|---|---|
| 5,290,383 A | | 3/1994 | Koshimizu |
| 5,394,092 A | * | 2/1995 | Wentworth et al. ........... 324/464 |
| 5,446,538 A | | 8/1995 | Noll |
| 5,781,289 A | | 7/1998 | Sabsabi et al. |
| 6,034,768 A | | 3/2000 | Fraser et al. |
| 6,635,105 B2 | | 10/2003 | Ahlborn et al. |
| 6,750,449 B2 | * | 6/2004 | Marcus ........................ 250/288 |
| 7,164,121 B2 | | 1/2007 | Hirano et al. |
| 7,393,385 B1 | * | 7/2008 | Coffey et al. ..................... 95/59 |
| 7,394,537 B1 | | 7/2008 | Lindfors et al. |
| 7,440,097 B2 | | 10/2008 | Benicewicz et al. |
| 7,778,007 B2 | * | 8/2010 | Kawato ......................... 361/254 |
| 7,821,634 B2 | | 10/2010 | Dillon et al. |
| 7,838,825 B2 | | 11/2010 | Vakhshoori et al. |
| 7,999,928 B2 | | 8/2011 | Beckstead et al. |
| 8,301,396 B1 | * | 10/2012 | Dhanijala et al. ............... 702/24 |
| 2005/0012038 A1 | * | 1/2005 | Marcus et al. ................ 250/288 |
| 2013/0321804 A1 | * | 12/2013 | Kulkarni et al. .............. 356/316 |

* cited by examiner

SPARK EMISSION PARTICLE DETECTOR

CROSS REFERENCE TO RELATED APPLICATIONS

This patent document claims the priority of U.S. Provisional Application No. 61/391,478, filed Oct. 8, 2010, entitled "SPARK EMISSION PARTICLE DETECTOR." The entire content of the before-mentioned patent application is incorporated by reference as part of the disclosure of this application.

BACKGROUND

This patent document relates to devices and techniques for particle composition analysis.

Various methods for particle analysis involve impaction and collection of airborne particles on a filter, and subsequent analysis. The analysis can be achieved in various ways, including chemical digestion and subsequent analysis by atomic absorption spectroscopy, inductively-coupled plasma optical emission spectroscopy, inductively-coupled plasma mass spectrometery, measurements with a scanning electron microscope, or measurements with a transmission electron microscope.

Real-time particle composition analysis can be achieved by using an aerosol mass spectrometer which analyzes bulk particles, and an aerosol time-of-flight mass spectrometer which analyzes single particles. In either case, particles are drawn through an orifice or aerosol lens into a particle beam, in which they are partially or completely vaporized using any one of several methods. Ions from the vaporization process are detected to infer the composition of particles from the ion fingerprint. Laser-induced breakdown spectroscopy can also be used to measure aerosols, either singly or in bulk. In these instruments, analysis can be real-time or nearly real-time. Many implementations of such instruments tend to be expensive and physically large, and complex.

Researchers at the National Institutes of Occupational Safety and Health attracted particles to a charged pin, and performed laser-induced breakdown spectroscopy to create a plasma to vaporize the attracted particles, exciting atomic emission that provides information about the composition of the particles. This approach can provide simplicity of concentrating the particles and good analysis results. The approach does rely upon a laser, which may present optical hazards, requires maintenance by skilled technicians, and other complications, and also may lack electrical and efficient aerodynamic focusing.

SUMMARY

Techniques, structures, apparatus and materials are disclosed for implementing particle detection.

In one aspect, a device for detecting particles includes a gas flow chamber to receive aerosol particles and carry the received aerosol particles a stream of gas or gas mixture; an aerosol charger to place an electrostatic charge on the aerosol particles carried in the stream of gas or gas mixture; a collection electrode downstream from the aerosol charger to attract the charged particles in response to a received initial voltage and polarity; a power supply to charge to the collection electrode to the initial voltage and polarity to cause the collection electrode to attract the charged particles; a grounding electrode to provide an electrical flow to produce a spark discharge on the collection electrode; and an optical detector that receives light emitted by the spark discharge and detect a property of the particles from the received light.

In another aspect, a method for detecting particles can include receiving particles at an aerosol inlet of a detector; carrying the received particles within a stream of gas; charging the particles within the stream of gas using a charger to have a charge; transporting the charged particles to the location of a collection electrode; biasing the collection electrode to a voltage using a high-voltage apply to attract either negatively or positively charged particles; and analyzing the charged particles to determine a property of the particles.

In yet another aspect, a device for detecting particles can include an aerosol inlet to receive airborne aerosol particles; a gas flow chamber to carry the received aerosol particles in a stream of gas or gas mixture; an aerosol charger to place an electrostatic charge on the aerosol particles carried in the stream of gas or gas mixture; a transport component to convey the aerosol particles to the vicinity of a downstream collection electrode; the collection electrode to attract the charged particles in response to a received initial voltage and polarity; a power supply to charge to the collection electrode to the initial voltage and polarity to cause the collection electrode to attract the charged particles; a grounding electrode to provide an electrical flow for a spark discharge of the collection electrode; and an optical detector that receives light emitted by the spark discharge and detect a property of the particles from the received light.

The subject matter described potentially can provide one or more of the following advantages. The described techniques and apparatus for spark emission particle detection can be used to measure aerosol composition and improve upon all of the current methods, concentrating the aerosol particles and using simpler instrumentation than previous methods. This new combination of components can yield significant advantages for aerosol measurement. Also, the real time analysis possible with the described particle emission particle detector can reduce the analysis time and cost related to analytical equipment.

BRIEF DESCRIPTION OF THE DRAWINGS

Like reference symbols and designations in the various drawings indicate like elements.

DETAILED DESCRIPTION

Techniques and devices are described for implementing a spark emission particle detector. In one aspect, airborne aerosol particles can be concentrated in space, and their chemical composition can be analyzed once sufficient particles have been collected. Among other features, the described techniques and devices can be implemented in ways that provide particle detection in a compact size with simplicity of collection, a robust plasma generator with no optical hazards, and easily variable collection time to optimize signal.

Figure 1:
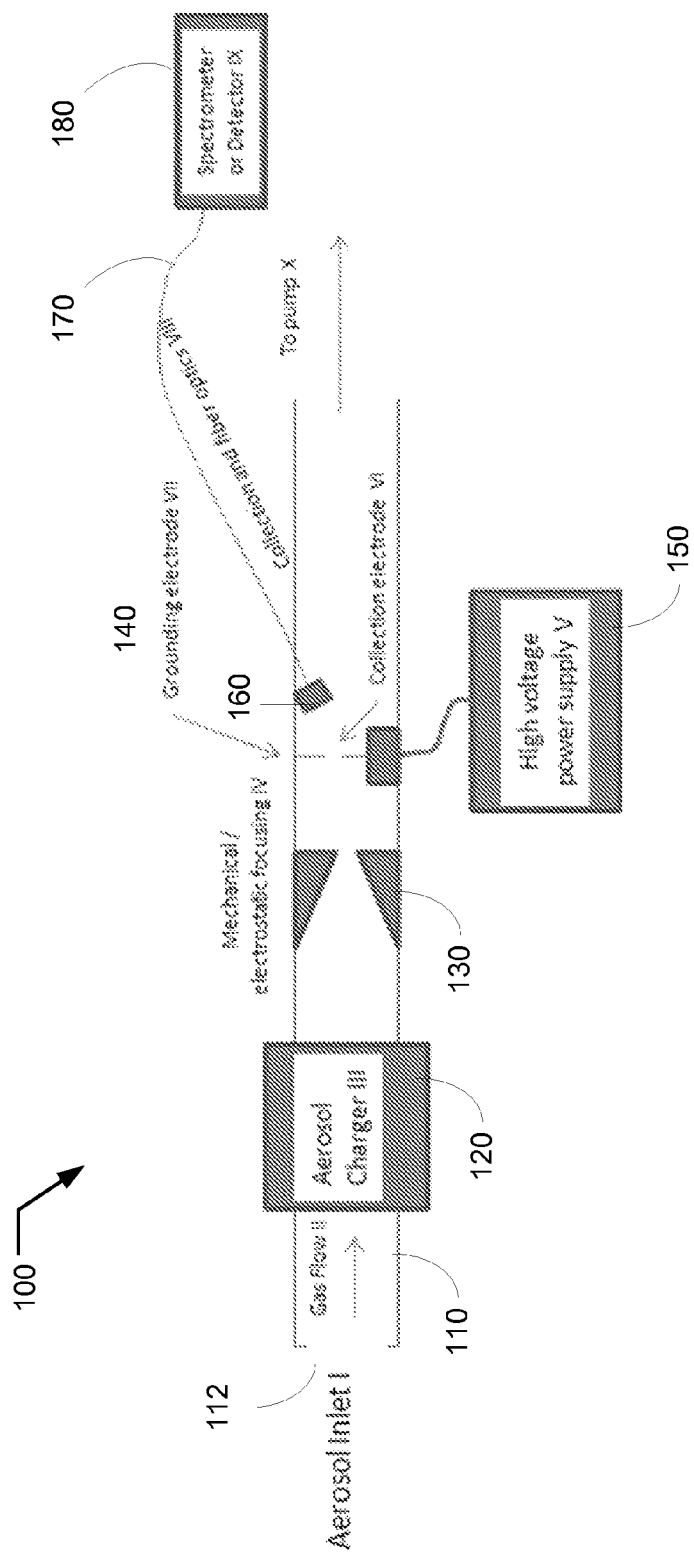
FIG. 1 shows a schematic of an exemplary spark emission particle detector.

FIG. 1 shows a schematic of an exemplary spark emission particle detector 100. The detector includes a conduit or chamber 110 with an aerosol inlet 112 that allows airborne aerosol samples to enter the instrument 100. This aerosol inlet 112 may be a simple opening, a critical orifice, the exit of a reduced-pressure aerosol lens, or other opening.

The instrument 100 is operated to provide a gas flow in the conduit 110 to carry a stream of the aerosol samples from the inlet 112 to the other end of the conduit 110. For example, a pump may be coupled at the output end of the conduit 110 to create the gas flow from the inlet 112 to the output end. The pump, which may be located downstream of the detector 180, functions to pull sample gas through the instrument. In other configurations, a Venturi arrangement, a gas push, or other means could be used to direct gas through the instrument. The gas flow may include a gas or a gas mixture of two or more gases. The gas composition or mixture for the gas flow may be specifically chosen to enhance the detection plasma, for example, enriched in argon or helium.

The gas flow leads the stream of aerosol sample to an aerosol charger 120 that places an electrostatic charge on the aerosol particles in the stream of aerosol sample. The aerosol charger 120 can include a unipolar charger or a bipolar charger. An example of a unipolar charger can include a charger using radioisotopes to charge particles, and an example of a bipolar charger can include a corona charger. Various implementations of unipolar or bipolar chargers may be used.

The aerosol particles having the electrostatic charge placed by the aerosol charger 120 are led to a mechanical and electrostatic focusing component 130 that more fully aligns the aerosol particles with a downstream collection electrode 140 which includes a grounding electrode and a collection electrode VI. This may be accomplished by using one or more of the following: a simple narrowing of the duct, sheath flow from the walls of the duct, charging the walls of the duct in opposite charge to the collection electrode VI to repel particles to be collected, or other mechanical and electrostatic means.

A high voltage power supply 150 is provided to charge the collection electrode to a sufficient initial voltage and polarity so as to attract and collect charged particles from the gas flow. A grounding electrode VII, spaced at a specific distance from the collection electrode, forms the other portion of a circuit with the high voltage power supply 150. At a predetermined or user-specified interval or time, the high voltage power supply 150 forms a high voltage pulse that causes a dielectric breakdown or spark between the collection electrode and the grounding electrode. The high voltage pulse may be of the same polarity as the initial voltage, or the polarity of the high voltage pulse may be reversed to quickly repel particles from the collection electrode that had been collected before creating a spark. The spark becomes an analytical plasma from which light can be collected and particle composition analyzed.

As shown, a collection optical unit 160, e.g., a lens or lens assembly, can be placed near the collection electrode to collect light produced by the emission spark. A collection fiber 170 can be used to direct the light collected by the collection optical unit 160 to the detection module 180, which can be, e.g., a spectrometer or an optical detector.

In operation, the collection electrode attracts charged particles in the gas flow for a user-defined period and thus concentrates the particles. A high voltage pulse generated by the high voltage power supply 150 later forms an analytical plasma between the collection electrode and the grounding electrode VII. The collection electrode can be of any one of various configurations, for example, a pin. A cleaning mechanism, including but not limited to reversing polarity, mechanical agitation, mechanical abrasion, or fluid pulsing, may be incorporated into the collection electrode.

As described above, the grounding electrode forms the other portion of a circuit during a spark discharge with the collection electrode VI and the high voltage power supply V. The grounding electrode can be of any configuration; one example is a pin.

Emission from the spark discharge is collected via collection optics 160 and/or fiber optics 170 for transmission to the spectrometer/detector 180. The collection optics 160 may be any optical elements including lenses, mirrors, and/or dispersive optical elements. The fiber optic 170 may be of any type able to transmit the emitted light to the spectrometer/detector 180. The fiber optic 170 may be omitted and the collected light can directly impinge on the spectrometer/detector 180. Alternatively, the collection optics 160 may be omitted and a bare fiber may be used to collect light. In other implementations, the spectrometer/detector 180 may be used to directly collect and detect the plasma spark without the collection optics or fiber as shown in FIG. 1.

The spectrometer/detector 180 functions to measure all or some portion of the wavelengths of light emitted by the plasma, to identify the composition of the particles entrained in the plasma. The detector 180 may be simple, such as one or more photodiodes or photomultiplier tubes with band pass filters to allow only particular wavelengths of light onto the detector, or the detector may be a dispersive spectrometer, such as of for example a Czerny-Turner, Paschen-Runge, or echelle design, with an array or camera detector.

As described above, particles entering the device 100 are charged and directed to collect on a collection electrode that is biased to attract particles of either a positive or negative charge. A high-voltage pulse forms plasma between the collection and grounding electrodes that involves the particles on the electrodes. Light emitted from the plasma contains information on the composition of the particles. The emitted light is collected for atomic or molecular spectroscopic analysis.

Figure 2A:
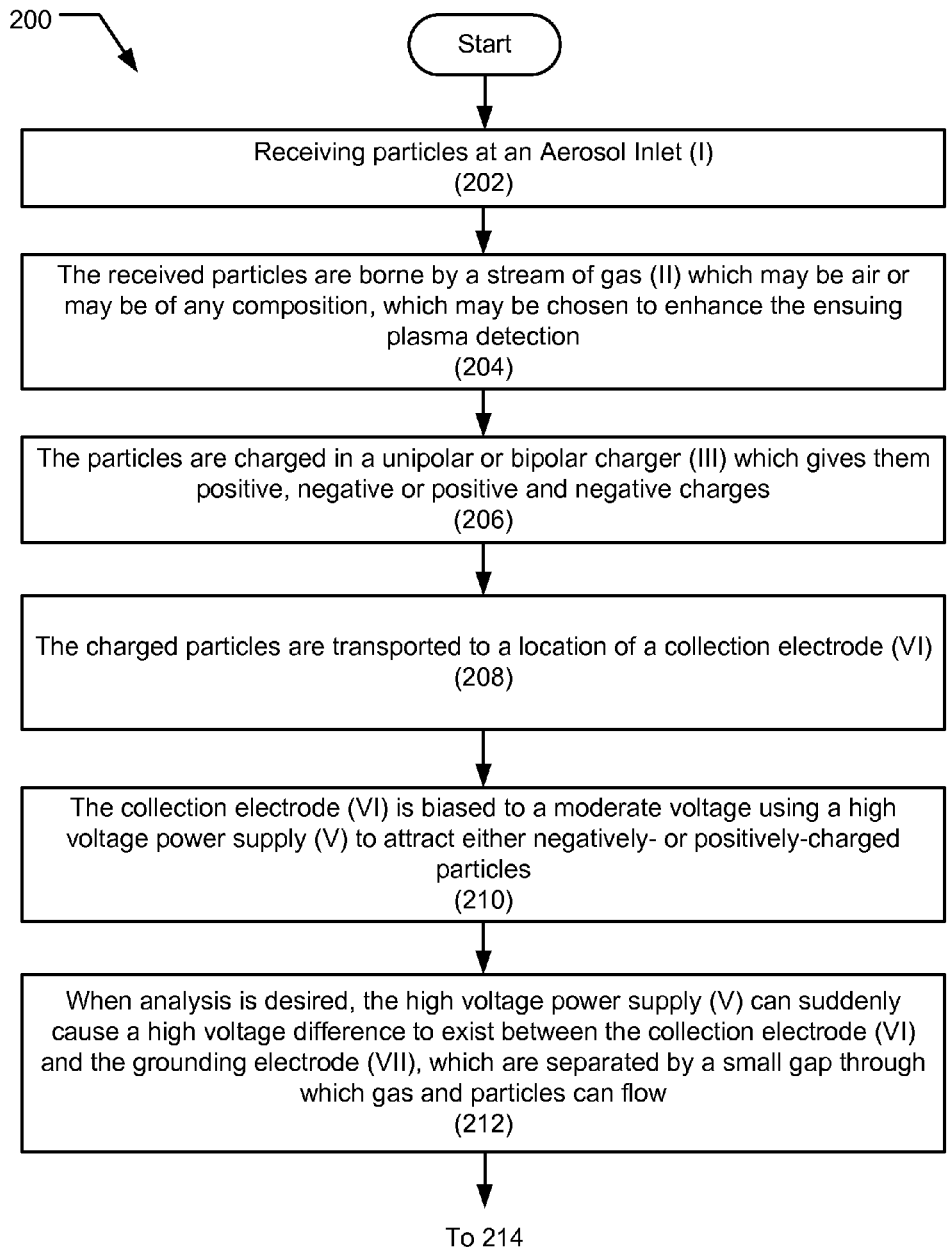
FIGS. 2A and 2B show a process flow diagram of a process describing an exemplary process of detecting particles.
Figure 2B:
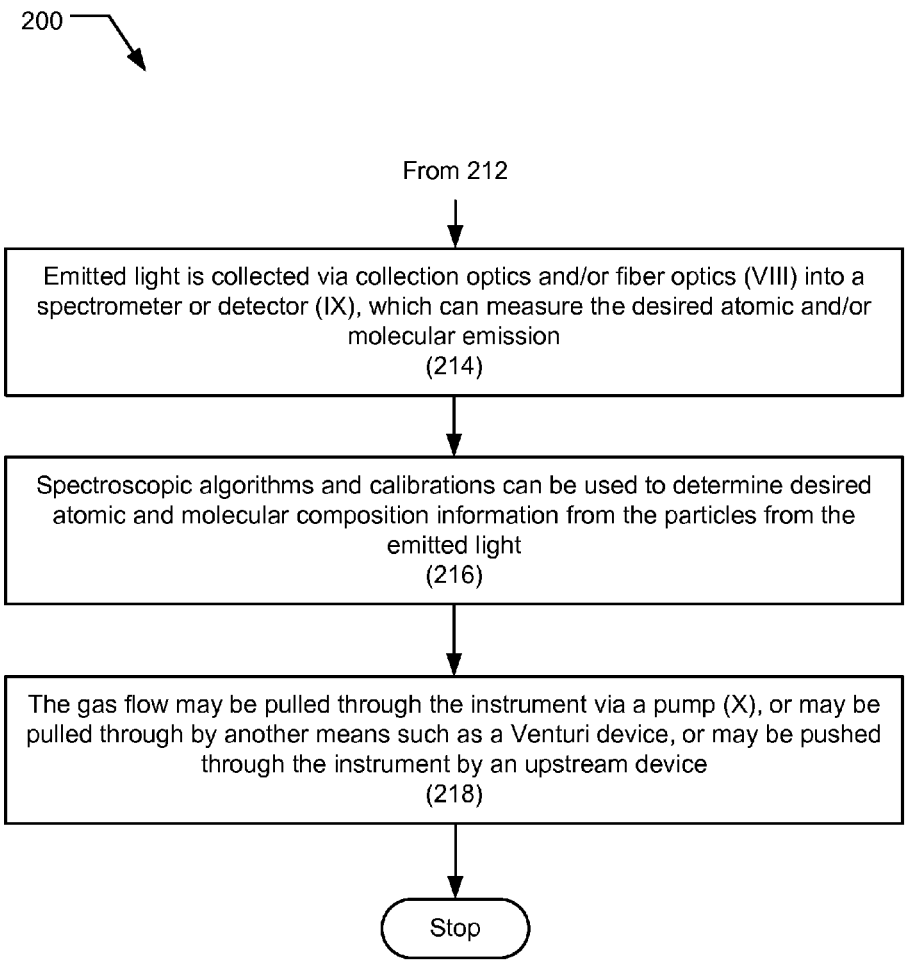

FIGS. 2A and 2B show a process flow diagram of a process 200 describing an exemplary process of detecting particles. A detector (e.g., detector 100) can receive particles at an Aerosol Inlet (I) (202). The received particles are borne by a stream of gas (II) which may be air or may be of any composition, which may be chosen to enhance the ensuing plasma detection (204). The particles are charged in a unipolar or bipolar charger (III) which gives them positive, negative or positive and negative charges (206). The charged particles are transported to a location of a collection electrode (VI) (208). Transporting the charged particles can be performed using a focusing mechanism to focus the particles mechanically and/or electrostatically to the location of the collection electrode (VI). The collection electrode (VI) is biased to a moderate voltage using a high voltage power supply (V) to attract either negatively- or positively-charged particles (210). When analysis is desired, the high voltage power supply (V) can suddenly cause a high voltage difference to exist between the collection electrode (VI) and the grounding electrode (VII), which are separated by a small gap through which gas and particles can flow (212). This can cause dielectric breakdown in the gap, forming plasma that can be used to analyze the particles which were collected on the collection electrode (VI). Emitted light is collected via collection optics and/or fiber optics (VIII) into a spectrometer or detector (IX), which can measure the desired atomic and/or molecular emission (214). Spectroscopic algorithms and calibrations can be used to determine desired atomic and molecular composition information from the particles from the emitted light (216). The gas flow may be pulled through the instrument via a pump (X), or may be pulled through by another means such as a Venturi device, or may be pushed through the instrument by an upstream device (218).

While this document contains many specifics, these should not be construed as limitations on the scope of any invention or of what may be claimed, but rather as descriptions of features that may be specific to particular embodiments of particular inventions. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Only a few implementations and examples are described and other implementations, enhancements and variations can be made based on what is described and illustrated.

What is claimed is:

1. A method for detecting particles, comprising:
   receiving particles at an aerosol inlet of a detector;
   carrying the received particles within a stream of gas;
   charging the particles within the stream of gas using a charger to have a charge;
   transporting the charged particles to the location of a collection electrode, the collection electrode being powered to an initial voltage and polarity with a high voltage power supply to attract and collect selected charged particles;
   biasing the collection electrode with a high voltage pulse having an absolute value greater than an absolute value of the initial voltage using the high-voltage power supply to cause a spark between the collection electrode and a ground electrode; and
   analyzing the spark to determine a property of the selected charged particles.

2. The method of claim 1, wherein charging the particles comprises:
   charging the particles using a charger that comprises a unipolar charger.

3. The method of claim 1, wherein charging the particles comprises:
   charging the particles using a charger that comprises a bipolar charger.

4. The method of claim 1, wherein charging the particles comprises:
   charging the particles to apply a positive charge.

5. The method of claim 1, wherein charging the particles comprises:
   charging the particles to apply a negative charge.

6. The method of claim 1, wherein charging the particles comprises:
   charging the particles to apply a positive charge and a negative charge.

7. The method of claim 1, wherein analyzing the particles comprises:
   using the high-voltage power supply to cause a high-voltage difference to exist between the collection electrode and the grounding electrode, creating a dielectric breakdown in the gas.

8. The method of claim 7, wherein analyzing the particles comprises:
   collecting emitted light of the spark using collection optics or fiber optics into a spectrometer or detector.

9. The method of claim 7, comprising:
   using spectroscopic algorithms and calibrations to determine desired atomic and molecular composition from the emitted light.

10. The method of claim 7, comprising:
    pulling the gas flow through measurement using a pump or pushing the gas flow by an upstream device.

11. The method of claim 1, wherein analyzing the selected charged particles comprises analyzing the selected charged particles in real time.

12. The method of claim 1, wherein transporting the particles comprises focusing the charged particles mechanically or electrostatically in a focusing device to direct the particles to a location of a collection electrode.

13. The method of claim 1, where the step of transporting the charged particles to the location of a collection electrode, further comprises:
    collecting the selected charged particles at the collection electrode for a user specified time prior to biasing the collection electrode with the high voltage pulse.

14. A device for detecting particles, comprising:
    an aerosol inlet to receive airborne aerosol particles;
    a gas flow chamber to carry the received aerosol particles in a stream of gas or gas mixture;
    an aerosol charger to place an electrostatic charge on the aerosol particles carried in the stream of gas or gas mixture to form charged particles;
    a transport component to convey the charged particles to the vicinity of a downstream collection electrode;
    a power supply to charge the downstream collection electrode to an initial voltage and polarity to cause the downstream collection electrode to attract selected charged particles, the power supply subsequently providing a high voltage pulse having an absolute value greater than an absolute value of the initial voltage to cause a spark discharge between the downstream collection electrode and a grounding electrode; and
    an optical detector that receives light emitted by the spark discharge and detects a property of the selected charged particles from the received light.

15. The device of claim 14, further comprising:
    collection optics to collect an emission from the spark discharge of the downstream collection electrode.

16. The device of claim 14, wherein the transport component comprises a focusing component to align the charged particles with the downstream collection electrode.

17. The device of claim 14, wherein the high voltage power supply charges the downstream collection electrode for a user specified time prior to providing the high voltage pulse.

18. A device for detecting particles, comprising:
    a gas flow chamber to receive aerosol particles and carry the received aerosol particles in a stream of gas or gas mixture;
    an aerosol charger to place an electrostatic charge on the aerosol particles carried in the stream of gas or gas mixture to form charged particles;
    a collection electrode downstream from the aerosol charger to attract selected polarity charged particles in response to a received initial voltage and polarity at the collection electrode from a power supply;
    a grounding electrode to provide an electrical flow between the collection electrode and the ground electrode to produce a spark discharge on the collection electrode in response to a high voltage pulse from the power supply, wherein an absolute value of the high voltage pulse is greater than an absolute value of the received initial voltage; and an optical detector that receives light emitted by the spark discharge and detects a property of the selected polarity charged particles from the received light.

19. The device as in claim 18, comprising:
a pump coupled to the gas flow chamber to cause the stream of the gas or gas mixture to flow.

20. The device of claim 18, wherein the power supply supplies the initial voltage and polarity for a user specified time prior to providing the high voltage pulse.

* * * * *